United States Patent
Gordon

Patent Number: 5,861,955
Date of Patent: Jan. 19, 1999

[54] TOPOGRAPHICAL CORNEA MAPPING FOR CORNEAL VISION CORRECTION

[75] Inventor: Eugene I. Gordon, Mountainside, N.J.

[73] Assignee: Medjet Inc., Edison, N.J.

[21] Appl. No.: 701,968

[22] Filed: Aug. 23, 1996

Related U.S. Application Data

[63] Continuation-in-part of Ser. No. 232,623, Apr. 25, 1994.

[51] Int. Cl.$^6$ ............................................. G01B 9/02
[52] U.S. Cl. ........................ 356/360; 356/357; 606/166
[58] Field of Search .................... 356/345, 357, 356/359, 360; 606/166, 167, 2–6

[56] References Cited

U.S. PATENT DOCUMENTS

| | | | |
|---|---|---|---|
| 3,930,505 | 1/1976 | Wallach | 128/305 |
| 4,538,608 | 9/1985 | L'Esperance , Jr | 128/303.1 |
| 4,721,379 | 1/1988 | L'Esperance | 128/303.1 |
| 5,459,570 | 10/1995 | Swanson et al. | 356/345 |
| 5,491,552 | 2/1996 | Knuttel | 356/360 |

*Primary Examiner*—Robert Kim
*Attorney, Agent, or Firm*—Graham & James LLP

[57] ABSTRACT

A method and device for highly accurate corneal topographical mapping and a device for effecting the mapping for use in effecting vision correction by removal of corneal tissue. The method and device involve use of a modified optical interferometer with directing of a coherent light beam, such as from a laser, to the anterior surface of a cornea; splitting the beam so that half the beam is directed to a reference object having a predetermined shape; capturing the reflected light from the cornea and the reference object so as to form an interference pattern; and using the interference pattern to determine deviations or displacements of the corneal surface from the known reference shape. The deviations are then utilized in corneal tissue removing procedures, such as RK, PRK and RLK, by determination of the extent and position of tissue removal. With a modified RLK procedure, the deviations are used in preparing an appropriate corneal template for use with a keratome using a high speed water jet as the cutting means.

11 Claims, 4 Drawing Sheets

TOPOGRAPHICAL CORNEA MAPPING FOR CORNEAL VISION CORRECTION

This is a continuation in part of co-pending application of Ser. No. 232,623, filed Apr. 25, 1994.

FIELD OF THE INVENTION

This invention relates to methods and devices used in measuring and mapping the anterior surface of a cornea for refractive and therapeutic surgery of the cornea.

BACKGROUND OF THE INVENTION

Various methods have been developed to reshape the refractive window of the human eye, the cornea, in order to correct for the typical vision defects. Among these are nearsightedness (myopia), with the unaccommodated nominal focusing plane falling before the retina; farsightedness (hyperopia), with focusing plane beyond the retina and the combination of defects known as astigmatism, in which the cornea has a toroidal shape and there is no plane of best focus. The most common methods for vision correction for these defects are spectacles, and contact lenses (hard, soft and gas permeable types) which provide the correct amount of refractive power to shift the unaccommodated focusing plane to its optimum position on the retina. Glasses and contact lenses, when made to a proper prescription, provide vision correction to an accuracy of about ±0.25 diopter and best visual acuity. However, glasses are worn externally and are sometimes perceived to be uncomfortable, inconvenient, or detracting from personal appearance. They may actually impede certain activities such as sports, photography (or other view finder activities), aircraft flying and the like. Spectacles are sometimes misplaced and can be difficult to find if the natural error is large, i.e., the misplacer can't see them to find them. Contact lenses sometimes are utilized where use of glasses has been considered to be undesirable, mostly for cosmetic reasons. Contact lenses however, entail problems of their own in terms of possible eye infection with misuse and the necessity for specialized and time consuming procedures required to maintain sterility and minimize contamination. More importantly, many people cannot tolerate the insertion of foreign objects on or in their eyes. Whereas spectacles can be taken off and put on again as necessary, contacts are much less convenient in this respect. Contact lenses also tend to be expensive compared to spectacles.

In response to a need for safe permanent correction of vision, without recourse to glasses or contact lenses, two major surgical methods of vision correction have evolved. The first, radial keratotomy (RK), involves surgical incision of the cornea, with deep radial cuts outside the vision zone which cause a roughly predictable flattening of the cornea and a reduction in refractive power thereof, suitable for correcting low levels of myopia. This is however, a major surgical procedure requiring considerable skill in order to achieve the desired refractive correction. Though undercorrection errors are correctable, overcorrections are not. Additionally, the refraction unpredictably progresses toward hyperopia over long periods of time, i.e., about ten years.

The second procedure is photo-chemical and thermal corneal ablation with an excimer laser (photo refractive keratectomy-PRK) which can be achieved by selectively ablating corneal tissue from the anterior surface of the cornea. This procedure is also predicated upon the characteristics of the cornea wherein refractive correction of vision deficiencies can be achieved by varying the front surface curvature of the cornea. These methods are effectively based on the fact that the anterior surface of the cornea provides 80% of the total refractive power of the human vision system, and the rest is provided by the posterior surface of the cornea (negative lens) and the internal crystalline lens. Accordingly, relatively small changes in corneal curvature can significantly affect the focusing ability of the eye. Because of the manner in which shaping has been produced to date, this method has been used only in flattening out the surface of the cornea (decrease of curvature) by selective removal of the corneal tissue closer to the beam axis, i.e., suitable only for correction of low or medium myopia and mild astigmatism. Increase of curvature, for correction of hyperopia, with peripheral ablation is possible but is more difficult, and is not yet approved by the FDA.

The cornea comprises a thin protective epithelial layer on top of the Bowman's membrane or layer, which in turn covers the corneal stroma which is the thickest layer. While the epithelium is regenerative, the Bowman's membrane and stroma are not. With ablative corneal tissue removal procedures such as PRK, the epithelium and Bowman's membrane are removed together with a portion of the stroma. Subsequently, the epithelium regenerates on the exposed outer surface of the cornea but directly on the stroma, since the Bowman's layer is not regenerated. Direct regrowth of the epithelium on the stroma can however cause an undesirable corneal haze which gradually dissipates over time. Haze is also produced by the healing of the endpoint stromal surface layers which are badly mutilated by the ablation process. The resulting corneal curvature increases with time, i.e., regresses unpredictably.

Both RK and PRK, because of inherent instabilities and error factors, are also usually not suitable for correction of myopia of more than −6 diopters and PRK is not currently approved for corrections other than myopia.

A third surgical procedure known medically as Keratomileusis in situ (KIS) and also as Refractive Lamellar Keratoplasty (RLK) preserves the epithelium and Bowman membrane and has been used for corrections of up to −20 diopters. In such procedure there is an initial surgical removal, with a micro-keratome, of a uniform thickness button or lenticule of corneal tissue of a thickness containing the epithelium layer (intact), Bowman's membrane (intact) and a portion of the stroma. The button or lenticule preferably remains hingedly attached at one point to the cornea. The lenticule is moved out of the way, the stroma bed is then surgically reshaped, as required, and the lenticule is replaced, usually with adequate adherence and healing of the stroma-stroma surfaces and with the epithelium and Bowman's membrane being preserved, leaving the cornea clear. It appears that the stroma-stroma healing of lenticule-stromal bed interfaces of the RLK procedure reduces wound healing instabilities, making this procedure the most suitable for large refractive corrections. It also minimizes haze.

However, despite the advantage of retention of visual acuity and healing stability, the procedure is not very favored since it is complex, requiring high intra-ocular pressure, is expensive, is usually inaccurate, with high dependency on the surgeon's skill, and it can cause irregular astigmatism. These factors can be attributed to the high sectility and relatively generally unsupported character of a cornea, which makes use of a scalpel, or even a conventional micro-keratome, difficult and highly subject to inaccuracies and irregularities.

In a procedure described in co-pending application Ser. No. 08/304,245, filed Sep. 12, 1994, a device is described for use in shaped removal procedures with or without a flap with greater ease and accuracy in effecting corneal vision corrections. The device, in one embodiment, comprises a shaped template member as a deformation means (with the template being adapted in shape for specific corneas and desired final shape), wherein the template is placed and centered on the anterior portion of the corneal tissue to be removed, whereby it comprises a shaped surface therein to which the anterior portion, to be removed, is adapted to be fitted and deformed by such fitting.

The deformation is predeterminately controlled, such that the surface to be cut, at the base of this anterior portion, assumes a planar configuration, which is accessible for the cutting thereof. The shaped surface of the template has a height relative to a plane at the base of the template equal to the computed difference, point by point, of the difference in height between the anterior and posterior surfaces of the portion of the corneal tissue which is to be removed. The computed difference takes into account geometrical distortion and tissue compression/or extension. As a result, the posterior surface of the lenticule to be removed (i.e. the surface to be cut) assumes the planar configuration.

For different surgical requirements of refractive corrections, a series or catalog (standard) set of templates of appropriately differing shape and dimensions may be used, though specifically adapted custom templates based on the topographic mapping, may be readily constructed, and are preferred.

The shape of the template for a given desired correction depends on the relative position of the cutting plane and it is necessary that these portions be well established. Typical circular template dimensions are 6 mm in diameter, with deviations of the surface from planarity of 150 microns or less conforming to normal corneal corrections or irregularities. Preferably the surface of the template which comes in contact with the cornea is micro-roughened to prevent corneal slippage and lateral movement during subsequent cutting and to enhance suction.

The cutting means, is described as being a round, high speed rectilinear water (or sterile saline solution) jet produced by a water pressure of between 3000 to about 20000 psi and typically between 15000 to 20000 psi. It has been shown that a small diameter water jet beam of this character provides a very smooth transverse cut in corneal tissue, with a smoothness and integrity similar to that of the original tissue surface. In addition, since the cut is transverse, with little or no force vector directly into the cornea, no hydration of the cornea is detected with this procedure. The diameter of the jet is typically 30 $\mu$m but even 75 $\mu$m jets are suitable. The scanning speed is 5–40 millimeters per second and the cut occurs in one second or less. It has been demonstrated that no blade produces a cut that is less damaging to the tissue and generally it is much more damaging. The total water usage is about one drop.

Corneas are never perfectly spherical and it is important that the deviations therefrom be accurately, topographically pre-determined for effecting appropriate refractive and therapeutic corrections, in any of the aforementioned procedures. With the modified lamellar keratoplasty procedure the determination is also necessary in forming the template.

In order to effect the requisite topographical measurements, and in view of the only 3% reflectivity of a typical cornea, it has been the practice to use various ultrasonic and modified optical methods in mapping the irregular topography of the anterior of the cornea, as a guide for effecting the reshaping of the cornea. The common methods of topographical mapping, such as use of ultrasonic-ranging even when computer aided (as disclosed in U.S. Pat. No. 4,721,379) have however generally entailed problems in providing the very accurate mapping required (changes on the micron level are required for effective reshaping and ultrasonic mapping does not always provide such degree of accuracy). Other methods, such as disclosed in U.S. Pat. No. 5,116,115, involve the more accurate optical reflective mapping, but, because of the inherent transparency of the cornea, the method disclosed therein requires use of invasive reflective cover materials which must be placed on and exactly conformed to the anterior surface of the cornea to provide reflectivity, to provide a modicum degree of accuracy. In these techniques the number of data points, or resolution, is substantially limited.

At present, in view of deficiencies in very accurate individual topographic mapping, as well as in inherent deficiencies in the corneal reshaping laser instrument, utilization of the excimer laser to provide refractive vision corrections has resulted in refraction corrections of myopia with an accuracy of only about ±1 diopter, far less than that obtainable with corrective external lenses.

Most of the corneal topography machines provide a map of local corneal curvature which directly relates to refractive power at the point where the curvature is determined. For accurate reshaping of the cornea it is necessary to have an elevation map. The curvature map can be derived from the elevation map but the reverse is not true. The basis for this is imbedded in the mathematics of curve fitting.

It is therefore an object of the present invention to provide an extremely accurate non-invasive reflective topographic mapping method and device, suitable for use with a nearly transparent cornea, in corneal reshaping.

It is yet another object of the present invention to provide such topographic mapping device and method for use in shaping a corneal template for reshaping the cornea by means of a keratome such as formed from a water jet.

These and other objects, features and advantages of the present invention will become more evident from the following discussion and drawings in which:

SHORT DESCRIPTION OF THE DRAWINGS

SUMMARY OF THE INVENTION

Figure 1:
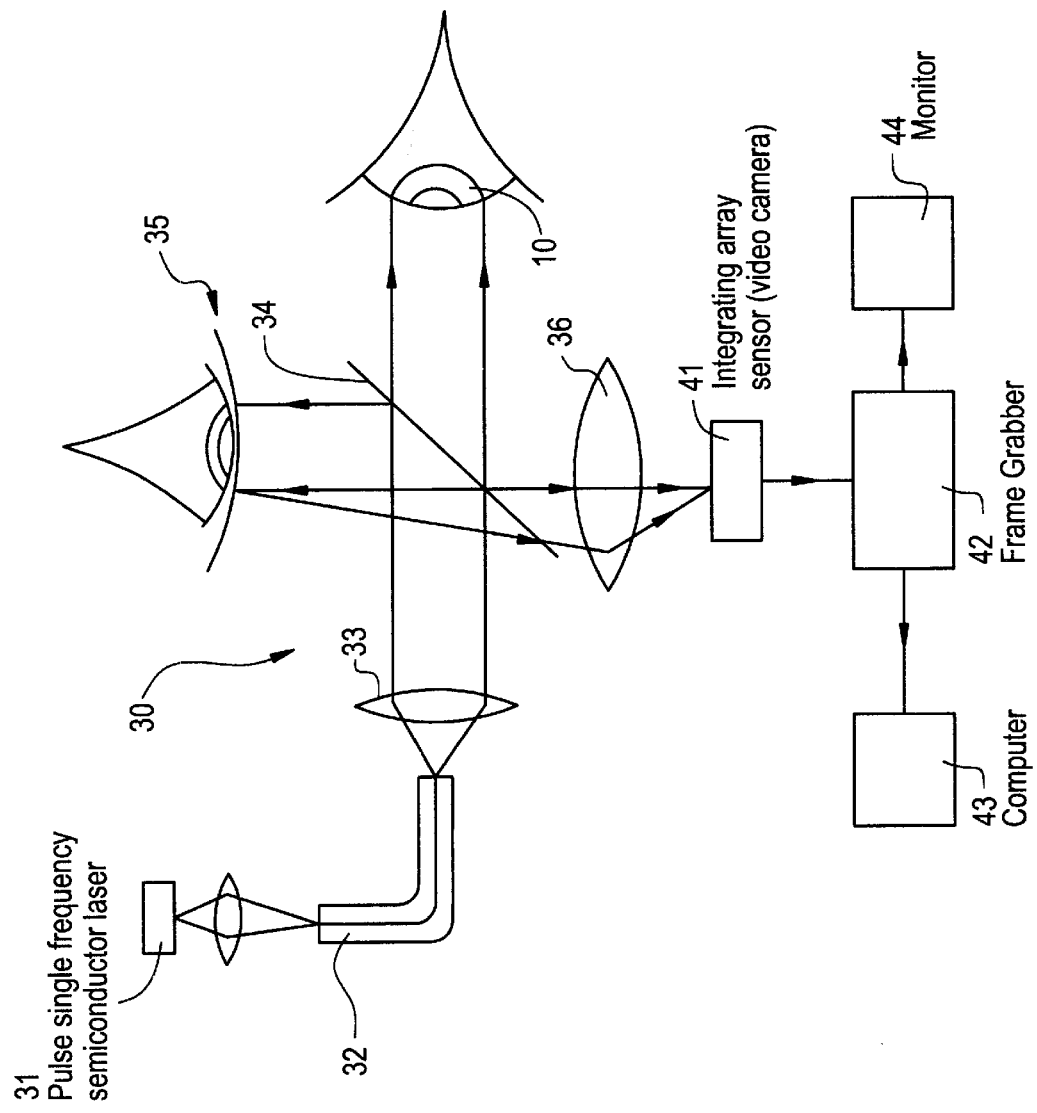
FIG. 1 depicts an apparatus for use in the accurate topological mapping of a cornea.

Generally the present invention comprises a method for corneal topographical mapping and a device for effecting the mapping, for use in effecting vision correction by removal of corneal tissue.

The method of the present invention comprises the steps of:

a) directing a spatially and temporally coherent light beam to illuminate the anterior surface of a cornea;

b) splitting the beam so that a portion, generally half, of the beam is also directed to illuminate a reference object having a predetermined shape (preferably a perfect sphere of known radius) and approximately the same reflectivity;

c) capturing the reflected light from the cornea and the reference object so that their images overlap forming an interference pattern; and recording the interference pattern and d) using the interference pattern to determine deviations of the shape of the cornea from the known reference shape.

The deviations are then utilized in corneal tissue removing procedures, as described above, to determine the extent and position of tissue removal. Such information may also be ideally utilized in directly controlling and effecting the tissue removal such as by computer control where feasible. The deviations may also be used in diagnosing corneal disease and other problems.

The device of the present invention comprises an optical interferometric system comprising:

1) a spatially and temporally coherent light source, such as a single frequency pulsed lowest order mode laser with pulses short enough so that the recorded images are not to be affected by eye movement and for eye safety consideration, with a wavelength preferably above 1.4 microns;

2) a beam splitter;

3) a predetermined reference shape such as a partially reflecting, perfect test sphere or a perfect flat;

4) capturing means, such as a video camera, for capturing reflected beams from the cornea and the reference object; and 5) means for forming a recorded image of an interferometric pattern showing a topographical map of the cornea and its deviation from the reference shape.

Sufficient light is specularly reflected from the cornea (probably because of its being wetted by tear film), despite its nearly transparent nature, to form a useful interferometric pattern.

DETAILED DESCRIPTION OF THE INVENTION

The optical interferometric system, such as a modified Twyman-Green interferometer, as used in the present invention, is based on interfering optical reflections of a collimated laser beam incident on both a test sphere (or equivalent, i.e., by using an applanatic lens in front of the cornea to make it appear to be flat and thus the reference surface may also be a flat) and a substantially transparent anterior corneal surface. The system produces a topographic map of the height difference between the cornea surface and the reference (surface or equivalent), at least in the intended area of corneal correction. The difference in height resolution is better than 0.775 microns and the horizontal resolution, using a video camera, is about 10–20 microns. The time to produce the image on a charge storage imaging device, with nominal beam power, is about 1 millisecond or less, so the eye is effectively stationary during the measurement. The system operates optimally with a smooth surface. Accordingly, though not necessary since the live cornea has a natural tear film which makes it smooth and shiny, i.e., a specular reflector, it may be desirable to apply a viscous liquid layer artificial tear film, such as of water or glycerin, to the cornea to enhance smoothness and reflectivity.

The interferometric system utilizes a beam splitter whereby a mirror image with respect to the beam splitter, of the spherical test surface (cornea) is superimposed on the real image of a reflecting reference surface of similar shape, producing an interference pattern constituting the topographical contour map. Modifications include the use of a pulsed laser and a video camera for capturing interference images, which would be otherwise lost because of minute eye movements. The interference of light reflected from the spherical test surface (cornea) and the reflective reference surface causes the production of interference contours superimposed on the image of the cornea. Successive open bright or dark contours correspond to longitudinal path differences, relative to the reference surface, by which the height and radius of curvature of the nominally spherical surface can be determined.

The elements of the interferometer, in a preferred embodiment, include a semiconductor laser of appropriate wavelength, a fiber guide which also functions as a spatial filter, and a first lens, for collimating the output beam of the optical fiber to a parallel beam of specified diameter. A 50% beam splitter sends half the energy to the spherical surface and the planar reflective surface, and it is the interference between the reflected beams which provides the contour pattern and the determination of the topography of the curved surface. This pattern, which is in the plane of the test surface, is viewed through a second lens, with a video camera, a frame grabber and a monitor. The video camera must be sensitive to optical radiation at the utilized wavelength. A camera based on a solid state imaging chip is desirable because of positional accuracy of each picture element and the ability to electronically control the integration period.

In use, the video system is put into an integrating, non-scanning mode, the laser is turned on, and the image is accumulated or integrated as charge on a storage surface of the imaging device. After a short fixed integration period, wherein the eye moves much less than half a wavelength, the laser is turned off and the image is scanned out as a single frame, is digitized and stored by a frame grabber. It is thereafter displayed as a still image on a conventional monitor.

It is important that the topographic system be initially properly aligned such as with the alignment marks such as may be lightly etched on the cornea in areas not involved with actual vision and the reference sphere is adjusted in the x, y and z coordinates so that it has the same axis as the cornea and has a bright full ring on the axis.

Corneal reshaping, by removal of cornea tissue, is with a maximum removal of about 150 microns of tissue depth from the 700 micron (peripheral) to 560 micron (center axis) thickness of the corneal tissue. The desired area of corneal shaping covers the maximum dilated pupil area of about 6 mm diameter. At least two marks are required for minimal alignment purposes. Achieved shaping is determined by a topography scan, deficiencies determined, and additional realignment and shaping sequences initiated. It is highly preferred that full scale topographical contour map measurements be made for increased accuracy.

The operation of a Twyman-Green interferometer, modified with the use of a pulsed laser, with pulses being short enough not to be affected by eye movement, and to minimize energy to the retina of the eye, in accordance with the present invention, provides a topographical map of the anterior surface of the cornea which can be at any stage of a corneal correction procedure, is utilized particularly for measuring surface height changes at the sub micron level to a height above an arbitrary plane. The optical interferometric system is utilized for such purpose in conjunction with a bright, spatially and temporally coherent sources such as a single frequency laser. For eye safety consideration the wavelength of the laser is above 1.4 microns, but could be in the visible part of the spectrum, and for economic considerations, commercially available imaging devices are preferably utilized. A short wave length visible imaging device is less expensive by far.

By coordinating corneal tissue layer removal and the topographic maps during various phases of the refractive correction procedure, both accuracy of the correction and safety of the procedure is achieved, to acceptable levels.

DETAILED DESCRIPTION OF THE DRAWING AND THE PREFERRED EMBODIMENTS

With specific reference to the drawings, in FIG. 1, Twyman-Green type optical interferometer apparatus 30 is utilized to provide instantaneous topographic map 40 of the anterior surface of cornea 10. A pulsed single frequency semiconductor laser 31, illuminates the cornea 10 with collimated light through single mode fiber optic guide 32 and lens 33, and does not otherwise affect the eye. Beam splitter 34 causes 50% of the directed laser light to reflect off cornea 10 and 50% off reference surface 35 of known curvature. The reflected light from the cornea 10 and reference surface 35 pass through lens 36 and the objects from which they originate interfere with each other to form an overlapped image with superimposed interference contours as topographic contour map 40 (shown in FIG. 2), as captured by video camera 41. Frame grabber 42 catches a single image and directs it to monitor 44 for display and to computer 43 for recordation and processing, with the computer being programmed to calculate an elevation calculate an elevation map of the cornea for appropriate tissue removal by tissue removal means for effecting said correction.

Figure 3:
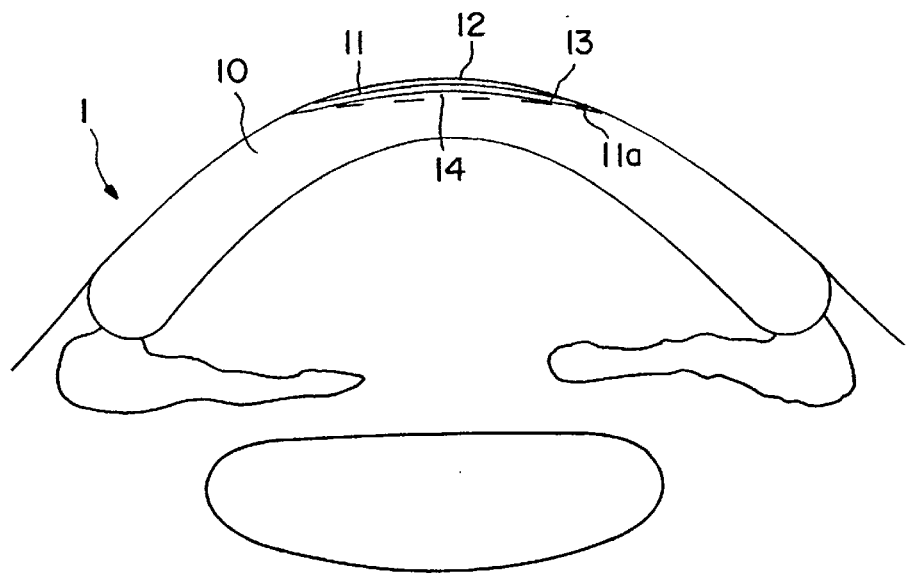
FIG. 3, is a human eye, shown in schematic cross section, with markings for calculated correction.

In FIG. 3, a human eye 1 is shown in schematic cross section. Portion 11 of the cornea 10, marked off with dashed lines, has been calculated and pre-determined as necessary to be removed for appropriate refractive vision correction with the topographic mapping information. However, the base 11a of the portion to be removed 11, has a curvature, which makes the accurate removal thereof, difficult to control. Portion 11 includes a section of the epithelium 12 and the Bowman's layer 13, as well as a segment of corneal stroma 14.

Figure 4:
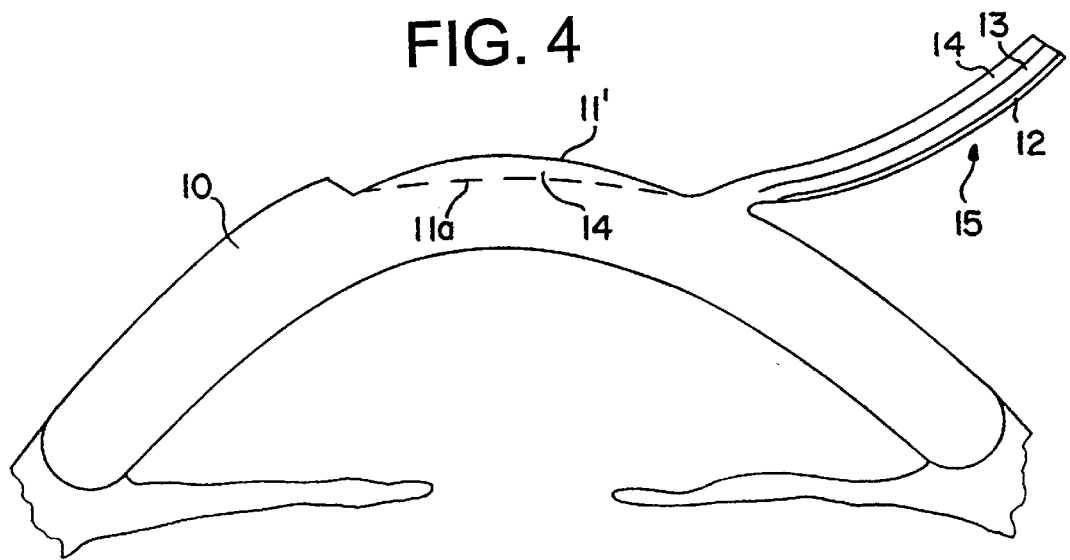
FIG. 4 illustrates the initial stage of the RLK type procedure.

FIG. 4 illustrates the RLK type procedure wherein a lenticular flap 15, of epithelium 12, Bowman's layer 13 and corneal stroma 14 are hingedly moved out of position and cornea 10 is shown with portion to be removed 11', for the refractive vision correction. In this embodiment, portion 11' is comprised only of a segment of the corneal stroma 14, though the base 11a still embodies a curvature.

Figure 2:
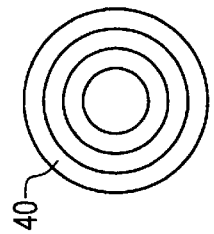
FIG. 2 is an example of a topographical map of the cornea as obtained by the mapping procedure shown in FIG. 1.
Figure 5:
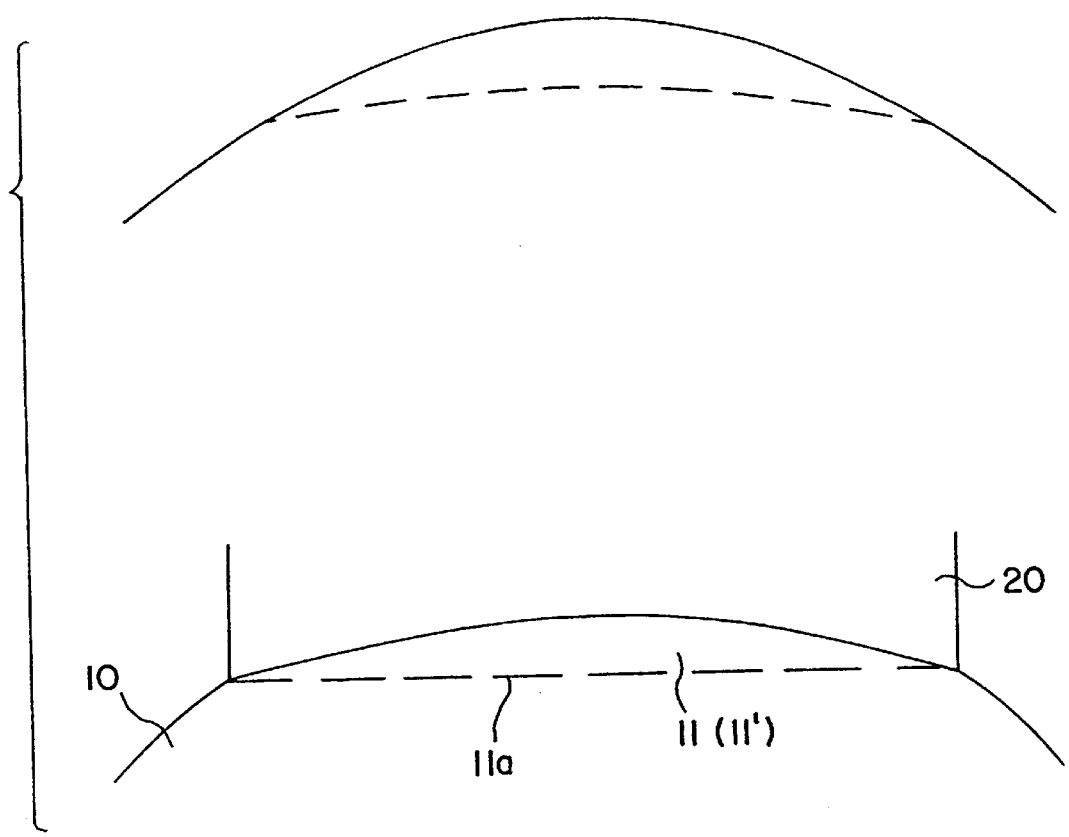
FIG. 5 depicts how a template is used in defining an appropriate planar cutting surface for cutting by a water-jet keratome.
Figure 6:
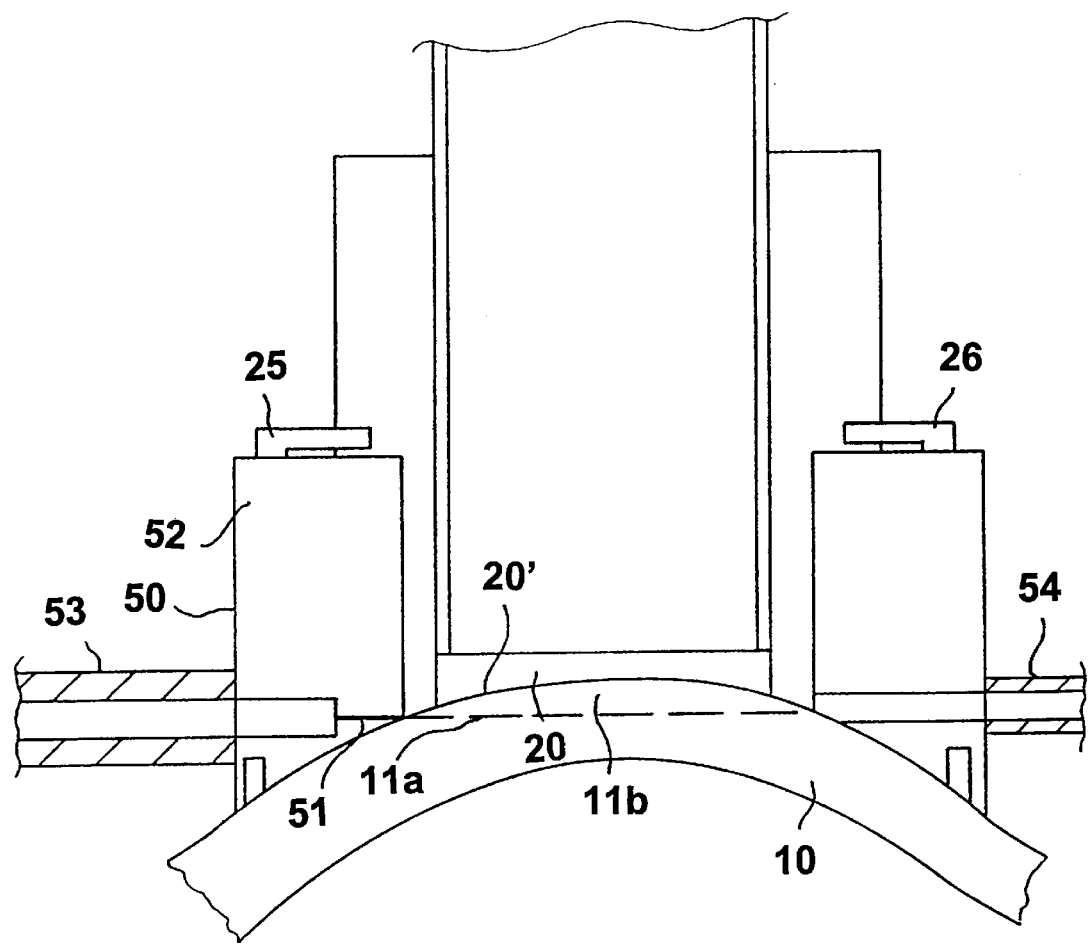
FIG. 6 depicts the procedure used in the planar cutting.

In FIG. 5, template 20 is applied to either portion 11 or more preferably to portion 11', to deform the portion, on which it is seated, to provide base 11a with a planar surface conformation, suitable for planar cutting as shown in FIG. 6. Templates are adapted to the type of correction (myopia, hyperopia, and astigmatism) and to the degree of correction required. The template 20, when fitted, cause the portion, to be removed, to be deformed such that an externally exposed planar surface for cutting is formed, as shown in FIG. 5, at the base of the template. The template is formed to conform to the actual corneal surface shape, as determined by the topographic mapping such as shown in FIG. 2, whereby the deformation is predeterminately controlled, such that the surface to be cut, at the base of this anterior portion assumes a planar configuration, which is accessible for the cutting thereof. The non-planar surface of the template has a height relative to a plane at the base of the template equal to the computed difference, point by point, of the difference in height between the anterior and posterior surfaces of the portion of the corneal tissue which is to be removed.

In FIG. 6, template 20, is shown as being positioned on cornea 10. Water jet cutting guide 50, is positioned relative thereto, such that planar surface 11a is exposed and aligned with water jet nozzle 51. The water jet cutting guide 50 is in the form of a ring 52 (and relative to the eye it is a globe fixation device), with water inlet 53, to nozzle 51, and water outlet 54. Template 20 is concentrically placed within the ring 52 and locked into position by locking tabs 25 and 26. To ensure that the deformation is effective in making the planar surface a true surface for cutting (i.e., wherein, after the cutting, the cornea relaxes into the desired configuration), a suction vacuum is applied through the porous template to cause the cornea surface 11b to become closely conformed to template inner surface 20'. The vacuum is maintained at least until the planar surface 11a has been cut.

After the cut is completed, the template and globe fixation device are removed from the cornea. If the cut is effected without an ALK procedure, the corneal correction is complete. If an ALK procedure has been utilized, the hinged lenticule is placed over the cut stroma tissue for healing in accordance with such known procedure.

It is understood that the above description and drawings are only illustrative of the present invention and that changes may be made in structure, components, procedures and the like, without departing from the scope of the present invention as defined in the following claims.

What is claimed is:

1. A method for corneal topographical contour mapping and corneal reshaping for vision correction, said method comprising the steps of:

a) directing a coherent light beam to the anterior surface of a cornea;

b) splitting the beam so that a portion of the beam is directed to a stationary reference object having a pre-determined shape and capturing reflected light from the reference object as an image of the surface of the reference object;

c) capturing the reflected light from the cornea as an image of the anterior surface of the cornea; bringing into coincidence the image of the cornea and the image of the reference surface and forming a recognizable interference pattern;

d) using the interference pattern to determine deviations of the anterior shape of the cornea from the known reference shape e) using the deviations to provide a topographical map of the cornea;

f) determining from said topographical map the degree of curvature of the anterior shape of the cornea necessary for said corneal reshaping for vision correction;

g) removing a portion of tissue with a tissue removal means, from the anterior of the cornea, which portion of tissue defines a deviation of said curvature of the anterior shape of the cornea from the anterior shape of the cornea of the topographical map, to effect the vision correction wherein the tissue removal means comprises a water jet and wherein the portion of the cornea comprising the deviation of said curvature of the anterior shape of the cornea from the anterior shape of the cornea of the topographical map is shaped by a template to provide a regular surface, wherein said water jet cuts along the regular surface to effect the vision correction.

2. A method for corneal topographical contour mapping and corneal reshaping for vision correction, said method comprising the steps of:

a) directing a coherent light beam to the anterior surface of a cornea;

b) splitting the beam so that a portion of the beam is directed to a reference object having a predetermined shape;

c) capturing the reflected light from the cornea; bringing into coincidence the image of the cornea and the image of the reference surface and forming a recognizable interference pattern; and d) using the interference pattern to determine deviations of the anterior shape of the cornea from the known reference shape, wherein a topographical contour map of the anterior surface of the cornea is obtained by directing a spatially collimated light from a pulsed narrow spectrum laser to the cornea through a beam splitter, which directs a portion of the light to the cornea and another portion of the light to a reflective surface of known curvature; and thereafter causing reflected light rays from the cornea and from the reflective surface to interfere with each other to form said contour topographical map, which is superimposed on the image of the cornea; and capturing the topographical map of the cornea with a video camera e) determining from said captured topographical map the degree of curvature of the anterior shape of the cornea necessary for said corneal reshaping for vision correction; and f) removing a portion of tissue with a tissue removal means, from the anterior of the cornea, which portion of tissue defines a deviation of said curvature of the anterior shape of the cornea from the anterior shape of the cornea of the topographical map, to effect the vision correction wherein the tissue removal means comprises a water jet and wherein the portion of the cornea comprising the deviation of said curvature of the anterior shape of the cornea from the anterior shape of the cornea of the topographical map is shaped by a template to provide a regular surface, wherein said water jet cuts along the regular surface to effect the vision correction.

3. The method of claim 2, wherein said method comprises the further steps of capturing a single image of said topographical map from the video camera with frame grabbing means and wherein the frame grabbing means directs the image to a computer which is programmed to calculate an elevation map of the cornea for appropriate tissue removal by tissue removal means for effecting said correction.

4. The method of claim 2, wherein said regular surface is planar.

5. The method of claim 2, wherein said regular surface is any one of a spherical, toroidal, part of a prolate spheroid shape.

6. The method of claim 2, wherein said cornea is coated with a thin viscous layer of liquid prior to said directing of laser light to the cornea, to enhance reflectivity thereof.

7. The method of claim 2, wherein said method further comprises the step of providing said eye with alignment means for alignment of tissue removal means therewith.

8. The method of claim 7, wherein the cornea is marked with said alignment marks, peripheral to the tissue of the cornea being removed.

9. A method for corneal contour mapping, for use in producing an elevation map of a cornea and derivation maps thereof, said method comprising the steps of:

(a) directing a spatially coherent beam of light to a beam splitter, comprising a partially transparent mirror, to produce two nominally identical beams which follow non-coincident paths;

(b) causing one of said identical beams to illuminate an anterior surface of the cornea to be mapped;

(c) causing the other of said identical beams to illuminate a stationary reference surface having a precisely predetermined shape;

(d) arranging, the beams, the anterior surface of the cornea and the reference surface, into a relative geometry such that an illuminated image of the anterior surface of the cornea overlaps an illuminated image of the reference surface, as observed through the beam splitter, wherein each of the anterior surface of the cornea and reference surface are in a position of a mirror image of the other; and wherein overlapping images have a superimposed interference pattern which directly measures displacement along the axis of the surface of one image from the other;

e) constructing an elevation map of the corneal surface from the interference pattern f) determining from said elevation map the degree of curvature of the anterior shape of the cornea necessary for said corneal reshaping for vision correction; and g) constructing, with a computer constructing means, a derivation map of the cornea with the reshaped curvature of the anterior shape of the cornea for use in defining a deviation of the curvature of the anterior shape of the cornea between the elevation map and the derivation map, which deviation is defined for the removal thereof by a tissue removal means wherein the tissue removal means comprises a water jet and wherein the portion of the cornea comprising the deviation of said curvature of the anterior shape of the cornea from the anterior shape of the cornea of the topographical map is shaped by a template to provide a regular surface, wherein said water jet cuts along the regular surface to effect the vision correction.

10. A device for topographical mapping of the anterior surface of a cornea for selective removal of tissue from the anterior of the cornea; said device comprising:

1) an optical interferometric system comprising:

i) a coherent light source, comprising a single frequency pulse laser with output pulses short enough not to be affected by eye movement and with a wavelength above 1.4 microns;

ii) a beam splitter;

iii) a predetermined reference shape;

iv) capturing means for capturing reflected beams from the cornea and the reference object as the respective images thereof; and v) means for forming an interferometric pattern between the captured respective images showing a topographical map of the cornea and its deviation from the reference shape 2) means for determining a desired shape of the anterior of the cornea and the deviation of the desired shape from the anterior of the cornea in said topographical map for removal by a corneal tissue removal means wherein the tissue removal means comprises a water jet and wherein the portion of the cornea comprising the deviation of said curvature of the anterior shape of the cornea from the anterior shape of the cornea of the topographical map is shaped by a template to provide a regular surface, wherein said water jet cuts along the regular surface to effect the vision correction.

11. The device of claim 10, wherein said device for topographical mapping means comprises a Twyman-Green interferometer, a pulse laser of single frequency, which provides the collimated light to said interferometer, a video camera for grabbing interfering light images from reflected light from the cornea and from a reflecting surface of known curvature, which interfering light images comprise said map as a topographical contour map and a frame grabber for grabbing individual images of the topographical contour map.

* * * * *